US008431754B2

(12) United States Patent
Sawant et al.

(10) Patent No.: US 8,431,754 B2
(45) Date of Patent: Apr. 30, 2013

(54) PROCESS FOR NITROALKANE RECOVERY BY AQUEOUS PHASE RECYCLE TO NITRATION REACTOR

(75) Inventors: Mahesh Sawant, Pune (IN); Daniel M. Trauth, Crystal Lake, IL (US); John G. Pendergast, Jr., Lake Jackson, TX (US)

(73) Assignees: Dow Global Technologies LLC, Midland, MI (US); ANGUS Chemical Company, Buffalo Grove, IL (US)

( * ) Notice: Subject to any disclaimer, the term of this patent is extended or adjusted under 35 U.S.C. 154(b) by 186 days.

(21) Appl. No.: 12/879,824

(22) Filed: Sep. 10, 2010

(65) Prior Publication Data

US 2011/0092748 A1    Apr. 21, 2011

(30) Foreign Application Priority Data

Oct. 20, 2009    (IN) ............................. 2539/CHE/2009

(51) Int. Cl.
C07C 205/00    (2006.01)
(52) U.S. Cl.
USPC .......................................... 568/947; 568/948
(58) Field of Classification Search .................. 568/947, 568/948
See application file for complete search history.

(56) References Cited

U.S. PATENT DOCUMENTS

| | | | |
|---|---|---|---|
| 1,967,667 A | 7/1934 | Hass et al. |
| 2,343,534 A | 3/1944 | Cavanaugh et al. |
| 2,418,241 A | 4/1947 | Stengel et al. |
| 2,455,425 A | 12/1948 | Levy et al. |
| 2,465,959 A | 3/1949 | Tindall |
| 2,489,320 A | 11/1949 | Nygaard et al. |
| 2,491,919 A | 12/1949 | Egiy |
| 2,511,454 A | 6/1950 | Bishop et al. |
| 2,512,587 A | 6/1950 | Stengel |
| 2,575,855 A | 11/1951 | Stengel et al. |
| 2,654,658 A | 10/1953 | Marshall |
| 2,654,788 A | 10/1953 | Marshall |
| 2,789,136 A | 4/1957 | O'Hara |
| 2,844,634 A | 7/1958 | McKinnis |
| 3,035,100 A | 5/1962 | Kirby et al. |
| 3,133,124 A | 5/1964 | Bonfield |
| 3,173,961 A | 3/1965 | Drimus et al. |
| 3,657,364 A | 4/1972 | Crawford et al. |
| 3,780,115 A | 12/1973 | Lhonore et al. |
| 3,869,253 A | 3/1975 | Lhonore et al. |
| 3,917,705 A | 11/1975 | Swanson et al. |
| 4,313,009 A | 1/1982 | L'honore et al. |
| 4,329,523 A | 5/1982 | James et al. |
| 4,394,220 A | 7/1983 | Egly et al. |
| 4,458,094 A | 7/1984 | Sherwin |
| 4,476,336 A | 10/1984 | Sherwin |
| 4,518,811 A | 5/1985 | Lhonore et al. |
| 4,626,607 A | 12/1986 | Jacquinot et al. |
| 2011/0028731 A1 | 2/2011 | Trauth et al. |
| 2011/0028732 A1 | 2/2011 | Trauth et al. |
| 2011/0092737 A1 | 4/2011 | Trauth |
| 2011/0092749 A1 | 4/2011 | Sawant et al. |
| 2011/0092750 A1 | 4/2011 | Trauth et al. |
| 2011/0160496 A1 | 6/2011 | Sawant et al. |

FOREIGN PATENT DOCUMENTS

| | | |
|---|---|---|
| EP | 0151074 A2 | 8/1985 |
| EP | 0171052 A2 | 2/1986 |
| GB | 916954 | 1/1963 |
| WO | WO2009/129099 | 10/2009 |
| WO | WO2011049681 | 4/2011 |
| WO | WO2011049682 | 4/2011 |
| WO | WO2011049683 | 4/2011 |
| WO | WO2011078931 | 6/2011 |

OTHER PUBLICATIONS

PCT International Search Report, PCT International Application No. PCT/US2010/048487, mailed Feb. 28, 2011.
PCT Written Opinion of the International Preliminary Examining Authority, PCT International Application No. PCT/US2010/048487, mailed Oct. 18, 2011.
PCT International Preliminary Report on Patentability, PCT International Application No. PCT/US2010/048487, mailed Feb. 20, 2012.
PCT International Search Report and Written Opinion, PCT International Application No. PCT/US2010/048487, mailed Feb. 28, 2011.
PCT Written Opinion of the International Preliminary Examining Authority, PCT International Application No. PCT/US2010/048482, mailed Oct. 18, 2011.
PCT International Preliminary Report on Patentability, PCT International Application No. PCT/US2010/048482, mailed Jan. 24, 2012.
PCT International Search Report and PCT Written Opinion, PCT International Application No. PCT/US2010/048482, mailed Nov. 17, 2010.
Albright, Lyle F., Nitration of Paraffins, Chemical Engineering, Jun. 6, 1966, pp. 149-156.
Olujic Z. et al., "Equipment improvement trend in distillation", Chemical Engineering and Processing, vol. 48, Mar. 26, 2009, pp. 1089-1104.
PCT Written Opinion of the International Preliminary Examining Authority, PCT International Application No. PCT/US2010/057628, mailed Feb. 14, 2012.
PCT International Preliminary Report on Patentability, PCT International Application No, PCT/US201048480, mailed May 3, 2012.
PCT International Search Report, PCT International Application No. PCT/US2010048480, mailed Mar. 2, 2011.
PCT International Preliminary Report on Patentability, PCT International Application No. PCT/US2010/057628, mailed Jul. 6, 2012.
PCT Written Opinion of the International Preliminary Examining Authority, PCT International Application No. PCT/US2010/057628, mailed Apr. 4, 2012.
PCT International Search Report and Written Opinion, PCT International Application No. PCT/US2010/057628, mailed Mar. 31, 2011.
Reply to Written Opinion, PCT International Application No. PCT/US2010/048482, filed Aug. 16, 2011.
Reply to Written Opinion, PCT International Application No. PCT/US2010/048487, filed Aug. 16, 2011.
Reply to Written Opinion, PCT International Application No. PCT/US2010/057628, filed Oct. 19, 2011.
Office Action, U.S. Appl. No. 12/879,799, mailed Aug. 30, 2012.

*Primary Examiner* — Jafar Parsa
(74) *Attorney, Agent, or Firm* — McDonnell Boehnen Hulbert & Berghoff LLP

(57) ABSTRACT

Disclosed are a process and an apparatus for synthesizing nitroalkanes by reaction of a hydrocarbon feedstock with aqueous nitric acid. Energy and capital costs may be reduced by recycling a majority of the aqueous phase back to the reactor.

17 Claims, 1 Drawing Sheet

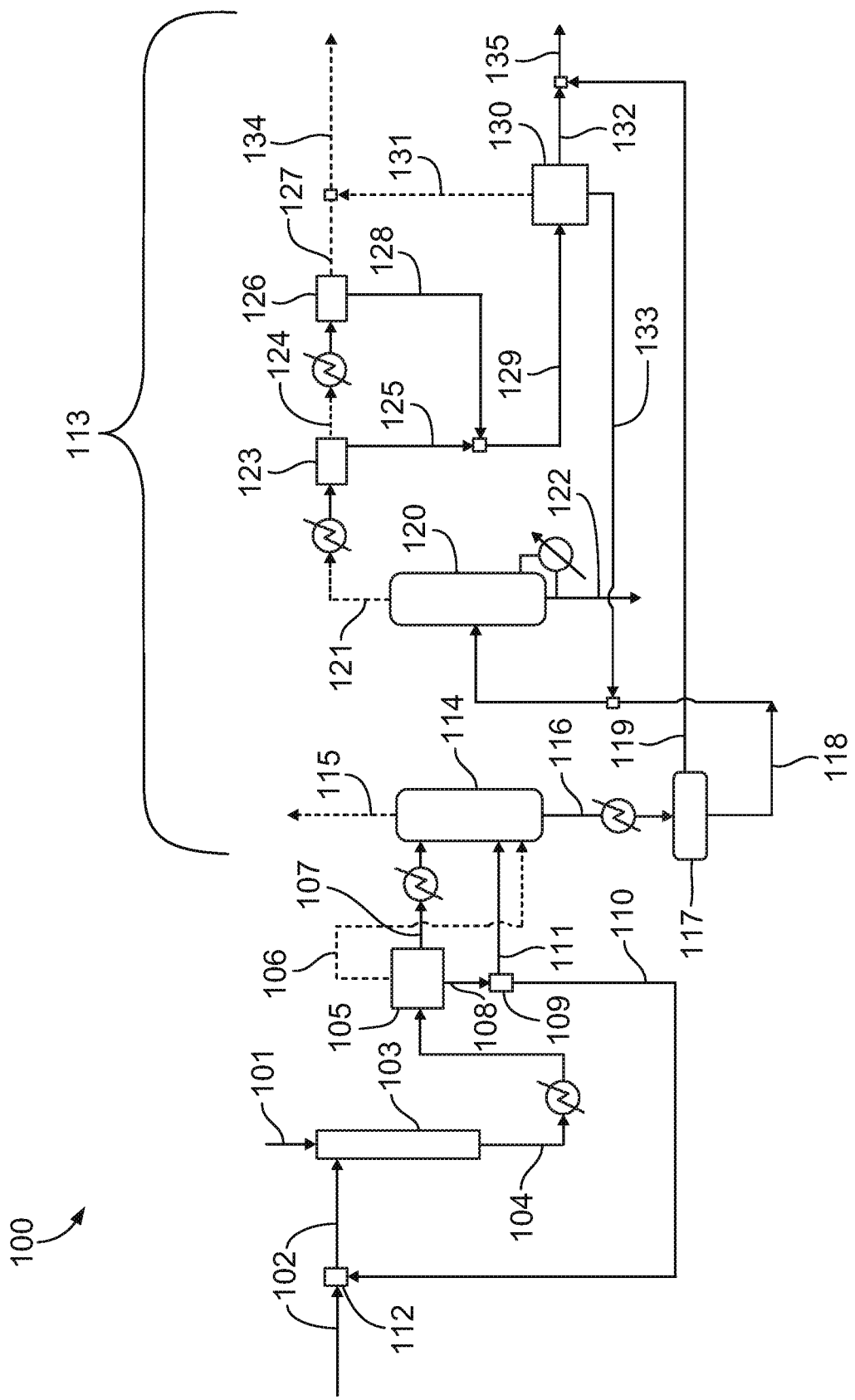

US 8,431,754 B2

PROCESS FOR NITROALKANE RECOVERY BY AQUEOUS PHASE RECYCLE TO NITRATION REACTOR

CROSS-REFERENCE TO RELATED APPLICATIONS

This application claims priority to Indian Provisional Application No. 2539/CHE/2009, filed Oct. 20, 2009, which is hereby incorporated herein by reference in its entirety.

FIELD

The invention relates to a process for synthesizing nitroalkanes. More specifically, the invention relates to a process for improved nitroalkane recovery in which an aqueous phase is recycled back to the nitration reactor.

BACKGROUND

The nitration of hydrocarbons generally involves the distillation of both an oil phase and an aqueous phase. However, this process requires large energy and capital expenditures.

In conventional vapor phase nitration schemes, described in U.S. Pat. Nos. 3,780,115 and 3,869,253, the reactor effluent is rapidly quenched and the quenched mixture is sent to a separator. The gas phase is then withdrawn for purification and recycling and the aqueous phase and the oil phase are separated by decantation and treated simultaneously to recover the desired nitroparraffin by distillation. New high pressure phase nitration processes use a lower strength nitric acid, resulting in a larger aqueous phase. Processing both the large aqueous phase and the oil phase is very energy-consuming. A need exists, therefore, for more economical and energy efficient processes for the manufacture of nitroalkanes.

BRIEF SUMMARY

In one aspect, a process is provided for synthesizing at least one nitroalkane. The process comprises: reacting a hydrocarbon feedstock with aqueous nitric acid in a reactor at a reactor pressure and a reaction temperature, such that a product stream comprising nitrated compounds and byproducts is formed; separating the product stream into at least an oil phase, a gas phase, and an aqueous phase, wherein the oil phase and the aqueous phase contain nitrated compounds; dividing the aqueous phase into a first aqueous stream and a second aqueous stream; returning the first aqueous stream to the reactor; and recovering the at least one nitroalkane from at least one of the oil phase and the second aqueous stream.

In another aspect, a process for synthesizing at least one nitroalkane comprises: reacting a hydrocarbon feedstock with aqueous nitric acid in a reactor at a reactor pressure and a reaction temperature, such that a product stream of nitrated compounds and byproducts is formed; quenching the product stream to separate the product stream into at least an oil phase, a gas phase, and an aqueous phase; dividing the aqueous phase into a first aqueous stream and a second aqueous stream; returning the first aqueous stream to the reactor; absorbing oil-soluble and water-soluble components from the gas phase into the oil phase and the second aqueous stream, respectively, to form a gas-recovered mixture; separating a gas-recovered aqueous phase from the gas-recovered mixture; and recovering the at least one nitroalkane from at least one of the oil phase and the second aqueous stream.

In yet another aspect, an apparatus for synthesizing at least one nitroalkane is provided. The apparatus comprises: a reactor for reacting a hydrocarbon feedstock with aqueous nitric acid to produce a reaction product stream; a cooling system for quenching the reaction product stream such that it phase separates into at least a gas phase, an oil phase, and an aqueous phase; a divider for dividing the aqueous phase into a first aqueous stream and a second aqueous stream; a recycling system for returning the first aqueous stream to the reactor; and a recovery system for recovering the at least one nitroalkane from at least one of the oil phase and the second aqueous stream.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 1 is a schematic diagram of the apparatus for synthesizing at least one nitroalkane, in accordance with an illustrative embodiment.

DETAILED DESCRIPTION

As noted above, in one aspect a process for synthesizing at least one nitroalkane is provided. One important advantage of this process is that it can recycle a majority of the aqueous phase as nitric acid diluent in the reactor without additional processing. The recycle may occur immediately after a reactor product stream is divided into an oil phase, a gas phase, and an aqueous phase. The solubility of nitropropanes (2-nitropropane and 1-nitropropane) in water is low and nitropropanes are significantly less reactive than propane. Thus, the presence of 2-nitropropane (in low concentration) in the aqueous phase returned to reactor does not affect the reactor performance significantly.

FIG. 1 illustrates an apparatus 100 for synthesizing at least one nitroalkane. A hydrocarbon feedstock 101 and aqueous nitric acid 102 may be introduced into a reactor 103. The hydrocarbon feedstock 101 and the aqueous nitric acid 102 may react at a reactor pressure and a reaction temperature, such that a product stream 104 comprising nitrated compounds and byproducts may be formed.

The hydrocarbon feedstock 101 and the aqueous nitric acid 102 may be mixed, or partially mixed, prior to entry into the reactor 103 or, alternatively; they may be added individually, with mixing to occur within the reactor 103. In addition, hydrocarbon feedstock 101 and the aqueous nitric acid 102, whether added together or individually, may be preheated prior to entry into the reactor 103.

In one example, the hydrocarbon feedstock 101 may consist essentially of propane and acetic acid. In other examples of the hydrocarbon feedstock 101 may include, without limitation, one or more of the following: alkanes and cycloalkanes (including alkyl substituted cycloalkanes), such as propane, isobutane, n-butane, isopentane, n-pentane, n-hexane, n-heptane, n-octane, 2,3-dimethylbutane, cyclohexane, cyclopentane, and methylcyclohexane; aryl alkanes such as ethylbenzene, toluene, xylenes, isopropyl benzene; 1-methylnaphthalene and 2-methylnaphthalene and 4-methylbiphenyl; fused cycloalkanes; alkyl substituted fused aryl compounds; fused cyclolalkane-aryl compounds (including alkyl substituted derivatives), such as tetralin, decalin, and methylnaphthalene; and carboxylic acids, such as acetic acid, propanoic acid, butanoic acid, and hexanoic acid. The nitration of reactants that already have one or more nitro substituents may also be contemplated, provided that the reactant still has an available hydrogen.

The aqueous nitric acid 102 may be delivered to the reactor 103 in the form of an aqueous solution that contains at least about 10 weight percent, preferably at least about 15 weight percent, more preferably at least about 20 weight percent, of the acid. Further, the solution may contain less than about 50 weight percent, preferably less than about 40 weight percent, and more preferably less than about 35 weight percent, of the acid. In other embodiments, the nitric acid solution may contain between about 15 and about 40 weight percent of the acid. In further embodiments, the nitric acid solution may contain between about 18 and about 35 weight of the acid.

The mole ratio of the hydrocarbon feedstock 101 to the aqueous nitric acid 102 may be at least about 0.3:1, more preferably at least about 0.5:1.

The reactor pressure may be at least about 500 psi (34 atm), more preferably at least about 1000 psi (68 atm), and further preferably at least about 1200 psi (82 atm). In some embodiments, the pressure may be about 1600 psi (109 atm) or less, preferably about 1500 psi (102 atm) or less, more preferably about 1400 psi (95 atm) or less. In other embodiments, the pressure may between about 1000 psi (68 atm) and 1400 psi (95 atm). Various methods known in the art may be used for maintaining the pressure within the desired range including, for example, through the use of a back-pressure regulator.

The reaction temperature within the reactor may be controlled (for example with heat exchange fluid or using heat generated from the reaction) to at least about 140 degrees Celsius and to less than about 325 degrees Celsius. In other embodiments, the temperature may be at least about 215 degrees Celsius and to less than about 325 degrees Celsius. In some embodiments, the temperature may be at least about 180 degrees, at least about 200 degrees, at least about 230 degrees, or at least about 240 degrees. In other embodiments, the temperature may be less than about 290 degrees, less than about 280 degrees, less than about 270 degrees, or less than about 250 degrees. In further embodiments, the temperature may be between about 200 and 250 degrees Celsius. In yet further embodiments, the temperature may be between about 215 and 280 degrees Celsius, or between about 220 and 270 degrees Celsius.

The residence time of the reactants in the reactor 103 may be preferably at least about 30 seconds, more preferably at least about 90 seconds. Residence time may be controlled in various ways including, for example, by the length and/or width of the reactor or through the use of packing material. Residence time may be determined by dividing the volume of the reactor by the inlet flow rates.

The reactor 103 may be a downflow configured reactor. That is, the reactor, which is preferably of an elongated and linear shape, such as a tube shape, may be positioned so that reactants are added through an entry port at or near the top of the reactor and then flow down the reactor for a residence time that is sufficient to allow reaction to occur and formation of the desired product. The product mixture may be collected through an exit port at or near the bottom of the reactor.

The operation of the reactor in a downflow configuration provides certain advantages over prior art systems, which generally utilize a horizontal, upflow, coiled or a batch autoclave type apparatus. In particular, the downflow configuration of the invention provides nitrated compounds that contain relatively low levels of oxidation byproducts as compared to such prior art systems.

Without wishing to be bound by any particular theory, it is believed that the advantages of the downflow reactor result primarily from its ability to minimize the amount and residence time of the liquid phase within the reactor. The liquid phase in general contains a low mole ratio of hydrocarbons to nitric acid. This low mole ratio favors oxidation chemistry at the expense of nitration and oxidation therefore primarily occurs in the liquid phase. In a downflow reactor (also referred to as a trickle bed reactor) the gas is the continuous phase and the liquid trickles down the reactor walls or packing. Therefore, the amount of liquid phase(s) in a downflow configured reactor is maintained at a low level and consequently oxidation chemistry is minimized.

In contrast, in an upflow reactor, also referred to as a bubble column, the liquid is the continuous phase (and bubbles rise quickly through the continuous liquid phase). Thus, an upflow reactor maximizes the liquid holdup. Because, as noted above, oxidation primarily occurs in the liquid phase, the upflow reactor maximizes the formation of oxidation byproducts. Similarly, coil and horizontal reactor configurations also increases liquid residence time and therefore oxidation chemistry as compared to a downflow reactor. A further disadvantage of coiled reactors is that they are not well-suited for industrial scale production because of the difficulty of fabricating large scale reactors in this shape.

The reactor 103 may also be packed with a packing material to improve reactant mixing and heat transfer and/or to vary the reactor volume. Packing of the reactor may be preferred, for example, in a propane nitration system where it is desired to increase the concentration of 2,2-dinitropropane in the product stream. Suitable packing materials may include, for example, glass beads, random packing, or structured packing, such as those typically employed in distillation devices. Other packing materials are known in the art and may be used. The reactor 103 may also be an un-packed reactor.

The product stream 104 then may enter a first cooling system 105. In the first cooling system 105, the product stream 104 may be quenched such that it separates into at least a gas phase 106, an oil phase 107, and an aqueous phase 108. One or more of the gas phase 106, the oil phase 107, and the aqueous phase 108 may contain nitrated compounds. The aqueous phase 108 then may enter a divider 109, which may divide the aqueous phase 108 into a first aqueous stream 110 and a second aqueous stream 111. The divider 109 may include at least one flow-meter to control the amount of the aqueous phase 108 in the first aqueous stream 110 and the second aqueous stream 111. The first aqueous stream 110 may then enter a recycling system 112. The recycling system 112 may mix the first aqueous stream 110 with the aqueous nitric acid 102 such that the first aqueous stream 110 dilutes the aqueous nitric acid 102 prior to entering the reactor 103. About 65 to 85 percent of the aqueous phase 108 may be returned to the reactor 103 through the recycling system 112. In an illustrative embodiment, a highly favorable energy and capital benefit may be obtained by returning 80 percent of the aqueous phase 108 to the reactor 103.

Further processing, such as distillation, may be carried out on the gas phase 106, the oil phase 107, and the second aqueous stream 111 to recover the at least one nitroalkane. For example, the gas phase 106, the oil phase 107, and the second aqueous stream 111 may enter a recovery system 113 for recovering the at least one nitroalkane from at least one of the oil phase 107 and the second aqueous stream 111. The recovery system 113 may comprise an absorber 114, a separator 117, and a stripping apparatus 120. The gas phase 106, the oil phase 107, and the second aqueous stream 111 may enter the absorber 114 for absorbing water-soluble and oil soluble components from the gas phase 106 into the oil phase 107 and into the second aqueous stream 111 to form a hydrocarbon gas stream 115 and a first gas-recovered mixture 116.

The first gas-recovered mixture 116 may enter the separator 117, for separating a gas-recovered aqueous phase 118 from the first gas-recovered mixture 116 to form a second gas-recovered mixture 119. The at least one nitroalkane may be recovered from either the second gas-recovered mixture 119 or the gas-recovered aqueous phase 118 or both. The at least one nitroalkane may be 2-nitropropane, 2,2-dinitropropane, or 1-nitropropane.

In an illustrative embodiment, the gas-recovered aqueous phase 118 may also be introduced into a stripping apparatus 120 to recover the at least one nitroalkane. The stripping apparatus 120 may divide the gas-recovered aqueous stream into at least a first top product 121 and a first bottom product 122. The first top product 121 may be introduced into a second cooling system 123 to provide at least a second top product 124 and a second bottom product 125. The second top product 124 may then be introduced into a third cooling system 126 to provide at least a third top product 127 and a third bottom product 128. The second bottom product 125 and the third bottom product 128 may be combined to form a fourth bottom product 129. The fourth bottom product 129 may enter a fourth cooling system 130 to produce at least a fourth top product 131, a middle product 132, and a fifth bottom product 133. The fourth top product 131 may combine with third top product 127 to form a fifth top product 134. The middle product 132 may combine with the second gas-recovered mixture 119 to produce a third gas-recovered mixture 135. The third-gas recovered mixture 135 may contain at least one nitroalkane, for example, 2-nitropropane, 2,2-nitropropane, or 1-nitropropane. The fifth bottom product 133 may be combined with the gas-recovered aqueous phase 118 and may be introduced into the stripping apparatus 120.

According to one embodiment, propane is reacted with aqueous nitric acid to form 2-nitropropane and other nitrated paraffins under the specific process conditions described herein. The reaction of propane with nitric acid may be carried out in a corrosion resistant reactor, such as a titanium reactor. The reactor is optionally surrounded by a shell with input and output ports for feeding a heat transfer fluid to the reactor. The heat transfer fluid, which can be, for example, an oil, allows the temperature of the reaction to be controlled to within the desired parameters.

It should be noted, however, that because the reaction between the nitric acid and propane is exothermic, use of a shell and a heat transfer fluid are not required. The temperature of the reaction can be regulated to be within the desired parameters by simply regulating the addition rate and/or concentration of the reactants.

EXAMPLES

Various examples are demonstrated using a computer simulation (for Examples 1 and 2) and a lab scale reactor (for Example 3 and 4).

The lab scale reactor is a single tube shell-and-tube heat exchanger with a thermowell located axially down the center of the reactor in order to determine the temperature profile along the reactor's length. The reactor is 46" long and has a shell which is 1.25" OD 304 stainless steel with a ½" OD (0.37" ID) type 2 titanium process tubing and a ⅛" OD (0.093" ID) type 2 titanium thermowell. A very fine, movable thermocouple is inserted into the thermowell for the temperature profile measurement. The thermowell can be removed and the reactor filled with packing. The reactor is mounted vertically. The nitric acid and propane reactant streams are mixed in a Swagelok® "T" fitting at room temperature prior to entering the reactor. Hot oil is fed to the reactor shell countercurrent to the reactants. The reactor effluent (reaction product) is cooled in a shell-and-tube heat exchanger using water as the coolant. The effluent is then depressurized with the gases and liquids collected, measured, and analyzed.

In Examples 3 and 4 below, the mass balance of the nitration reaction is determined by GC/MS for gases, aqueous, nitroparaffin oil, and scrubber liquids, Karl Fisher titration for water content, potentiometric titration for strong/weak acid quantification, and HPLC for weak acid identification and quantification.

Metrics shown in the Tables below are calculated as follows:

Nitric Acid conversion(%)=100×(Nitric Acid in−Nitric Acid out)/Nitric Acid in;

Propane conversion(%)=100×(Propane in−Propane out)/Propane in;

Nitric Acid yield=g nitric acid consumed/g nitroparaffins formed;

Organic yield=g propane and acetic acid consumed/g nitroparaffins formed;

1-nitropropane selectivity(%)=100×g 1-nitropropane/g nitroparaffins formed;

2-nitropropane selectivity(%)=100×g 2-nitropropane/g nitroparaffins formed;

Nitromethane selectivity(%)=100×g nitromethane/g nitroparaffins formed;

Nitroethane selectivity(%)=100×g nitroethane/g nitroparaffins formed.

Grams of nitric acid consumed is calculated by subtracting the moles of nitric oxide in the reaction product from the moles of nitric acid in the feed and then converting the number of moles to grams using the molecular weight of nitric acid.

Grams of nitroparaffins include: nitromethane, nitroethane, 1-nitropropane, and 2-nitropropane.

Example 1

Nitration Scheme without Aqueous Recycle

Propane is nitrated using 30 weight percent dilute aqueous nitric acid as the nitrating agent at the following process conditions: 1380 psi reactor pressure, 281.6 degrees Celsius reactor temperature, a residence time of 120 seconds, and a propane to nitric acid mole ratio of 1.5:1. A composition of a typical product stream from the reactor is summarized in Table 1.

TABLE 1

Reactor product stream composition
Temperature 281.6° C.
Pressure 94 atm

| Component | Mass fraction |
| --- | --- |
| Water | 0.682 |
| Carbon monoxide | 0.008 |
| Nitrogen | 0.004 |
| Nitric oxide | 0.028 |
| Nitrous oxide | 0.006 |
| Propane | 0.102 |

TABLE 1-continued

Reactor product stream composition
Temperature 281.6° C.
Pressure 94 atm

| Component | Mass fraction |
|---|---|
| Carbon dioxide | 0.016 |
| Acetone | 0.002 |
| Acetic acid | 0.049 |
| Nitromethane | 0.001 |
| Nitric acid | 0.019 |
| Nitroethane | 0.001 |
| Propionic acid | 0.006 |
| 2-nitropropane | 0.067 |
| 1-nitropropane | 0.006 |
| 2,2-dinitropropane | 0.003 |

The product stream is then quenched in an after-cooler to about 38 degrees Celsius and subsequently flashed into a gas phase, an aqueous phase, and an oil phase. The aqueous phase comprises almost all of the water along with the organic acids and the oil phase comprises the nitroalkanes along with propane and acetone. The aqueous/oil phase partition coefficients for the constituting species are given in Table 2.

TABLE 2

Aqueous/oil phase partition coefficients at 48° C. and 94 atm

| Component | $K_{aqu/oil}$ |
|---|---|
| Water | 91.517 |
| Carbon monoxide | 0.076 |
| Nitrogen | 0.032 |
| Oxygen | 2.377 |
| Nitrous oxide | 0.037 |
| Propane | 0.007 |
| Carbon dioxide | 23.069 |
| Nitrogen dioxide | 1.713 |
| Acetone | 0.107 |
| Acetic acid | 0.348 |
| Butane | 0.216 |
| Nitromethane | 0.118 |
| Nitric acid | 177.820 |
| Nitroethane | 0.032 |
| Propionic acid | 0.125 |
| 2-nitropropane | 0.009 |
| 1-nitropropane | 0.003 |
| 2,2-dinitropropane | 0.002 |

The gas phase, the aqueous phase, and the oil phase are then fed to an absorber, where the gas phase is steam stripped using medium pressure steam and the un-reacted propane and gas by-products are routed via the column overheads to the propane recovery section. The oil phase is absorbed in the aqueous phase and the resulting stream from the absorber is fed into a nitro-paraffin recovery column. The absorber is operated at a pressure of 147 psi (10 atm), equivalent to the operating pressure of the downstream propane recovery column. The nitro-paraffin recovery column is operated at a pressure of 22 psi (1.5 atm), where almost all the nitro-paraffins (along with around 3000 lb/h water) are obtained as overheads. The bottom stream from the nitro-paraffin recovery column is essentially water and dissolved acetic, propionic, and nitric acid. This stream, after exchanging heat with the resulting stream from the absorber, is then sent to intermediate water storage from where it is recycled as nitric acid diluent. The top stream from the nitro-paraffin recovery column containing nitroparaffins, water and non-condensables, is then routed through a series of cooler-decanter units, to condense and segregate nitroparaffins which are then sent to the nitropropane recovery section. The residual water recovered from the top stream is recycled back to the nitro-paraffin recovery column. A small amount of propane is recovered in the top stream of the nitro-paraffin recovery column. The resultant gas stream contains ~10 lb/h 2-nitropropane which is recovered in the tail-gas column by scrubbing with recycle water. The top stream from the tail-gas column is compressed to a pressure of 147 psi (10 atm) and routed to the propane recovery section. The aqueous scrubbing solution from the tail-gas column is recycled back to the absorber.

This high pressure process uses 15-30% dilute nitric acid. The nitration process generates around 3700 lb/h water which in addition to that used for nitric acid dilution amounts to water mass of ~52000 lb/h. The aqueous stream composition is given in Table 3.

TABLE 3

Aqueous stream composition
Temperature 49° C.
Pressure 94 atm

| Component | Mass fraction |
|---|---|
| Water | 0.889 |
| Carbon monoxide | 404 ppm |
| Nitrogen | 160 ppm |
| Nitric oxide | 218 ppb |
| Nitrous oxide | 0.002 |
| Propane | 0.009 |
| Carbon dioxide | 0.013 |
| Acetone | 0.002 |
| Acetic acid | 0.045 |
| Nitromethane | 0.001 |
| Nitric acid | 0.029 |
| Nitroethane | 222 ppm |
| Propionic acid | 0.003 |
| 2-nitropropane | 0.008 |
| 1-nitropropane | 223 ppm |
| 2,2-dinitropropane | 66 ppm |
| Methane | 2 ppm |

Example 2

Nitration Scheme with Aqueous Recycle

In an illustrative embodiment, at approximately the same process conditions as in Example 1, 75-85 percent of the aqueous stream coming out of the post-reactor flash is recycled to the nitration reactor as nitric acid diluent. The oil phase is cooled to 16 degrees Celsius before feeding to the absorber to reduce loss of nitropropanes in the overhead. The gas stream is steam stripped of all volatiles at a pressure of 44.1-73.5 psi (3-5 atm) and the resulting stream, which is essentially un-reacted propane and gas byproducts, is then compressed to a pressure of 147 psi (10 atm) in a two-stage compressor before routing it to the propane recovery section. The bottom stream from the absorber is cooled and phase-separated into an aqueous and an oil phase. The aqueous phase is further sent to the nitropropane recovery column which is operated at a pressure of 14.7 psi (1 atm) to recover the dissolved nitropropanes. Water, organic acids, and nitric acid are obtained as the bottom stream, whereas the top stream is cooled and decanted to obtain nitropropanes. Compared to the conventional scheme, the non-condensable stream is small and contains negligible amount of propane and 2-nitropropane, thus eliminating the need for the tail-gas recovery column.

The expected energy and capital requirement for a 2-nitropropane production rate of 5065.25 lb/h is estimated for both a no-recycle scheme and an aqueous recycle scheme, and compared in Table 4. The aqueous recycle option achieves almost similar 2-nitropropane recovery in the oil stream with an energy savings of 4.3 MMBTU/h in the nitropropane recovery column and 2.12 MMBTU/h in the heat exchanger, allowing elimination of the tail gas recovery column. Moreover, a smaller size nitropropane recovery column is required in the aqueous recycle scheme (2.1 ft. diameter) as compared to the conventional scheme (3.5 ft. diameter).

TABLE 4

Expected Energy and Capital requirement for aqueous recycle scheme as compared with the conventional scheme

|  |  | No-recycle Scheme | Aqueous Recycle Scheme |
|---|---|---|---|
| Absorber | Equilibrium stages | 10 | 11 |
|  | Column dia. (ft) | 2.20 | 2.20 |
|  | Pressure, atm | 10.00 | 3.20 |
|  | 250 psig steam, lb/h | 5930.00 | 5202.00 |
| Nitropropane recovery column | Equilibrium stages | 11 | 11 |
|  | Column dia. (ft) | 3.5 | 2.2 |
|  | Pressure, atm | 1.3 | 1 |
|  | $Q_{reboiler}$, MMBTU/h | 7.2 | 2.9 |
| Tail-gas recovery column | Equilibrium stages | 8 | — |
|  | Column dia. (ft) | 1 | — |
|  | Pressure, atm | 1.1 | — |
| Heat exchanger | No. of exchangers | 2 | 4 |
|  | Cooling duty, MMBTU/h | −4.4 | −2.28 |
| Compressor duty | MMBTU/h | 0.03 | 0.53 |
| Recovered oil phase composition | Water, lb/h | 44.4 | 37.1 |
|  | Nitrous oxide | 2.3 | 1.8 |
|  | Propane | 107.3 | 73.5 |
|  | Acetone | 117 | 114.4 |
|  | Acetic acid | 30.6 | 68.3 |
|  | Butane | 15.9 | 14.1 |
|  | Nitromethane | 61.6 | 61.7 |
|  | Nitroethane | 41.5 | 41.5 |
|  | Propionic acid | 7.4 | 16.23 |
|  | 2-nitropropane | 5062.8 | 5060.3 |
|  | 1-nitropropane | 459.6 | 459.6 |
|  | 1-nitrobutane | 0.4 | 0.4 |
|  | 2-nitrobutane | 1.6 | 1.6 |
|  | 2,2-dinitropropane | 215.1 | 215.1 |
| 2-nitropropane recovery |  | 99.95% | 99.90% |

Example 3

Propane Nitration with No Nitroparaffins in the Reactor Feed

Propane is reacted with 20 weight percent aqueous nitric acid with the above described reactor at a reactor pressure of 1400 psi (96.7 atm), a reaction temperature of 285° C., a residence time of 153 seconds, and a propane to nitric acid mole ratio of 1.81:1. The feed composition and the reaction product stream composition are summarized in Table 5.

TABLE 5

Feed composition and reaction product stream composition

| Component | Feed (g) | Reaction Product (g) |
|---|---|---|
| Propane | 1185 | 769 |
| Nitric Acid | 938 | 20.5 |

TABLE 5-continued

Feed composition and reaction product stream composition

| Component | Feed (g) | Reaction Product (g) |
|---|---|---|
| Water | 3728 | 4287 |
| Acetic Acid | 0 | 110 |
| Acetone | 0 | 11.1 |
| Nitromethane | 0 | 6.1 |
| Nitroethane | 0 | 4.3 |
| 2-nitropropane | 0 | 491 |
| 1-nitropropane | 0 | 75 |
| 2,2-dinitropropane | 0 | 8.0 |
| Nitric oxide | 0 | 48.5 |
| Nitrous oxide | 0 | 5.6 |
| Nitrogen | 0 | 12.7 |
| Carbon monoxide | 0 | 24.0 |
| Carbon dioxide | 0 | 221.7 |

Key performance metrics for this reaction are summarized in Table 6.

TABLE 6

Key performance metrics for nitration of propane with no nitroparaffins in the reactor feed

| Nitric acid conversion (%) | 97.8 |
|---|---|
| Propane conversion (%) | 35.1 |
| Nitric acid yield | 1.45 |
| Propane yield | 0.72 |
| Nitromethane selectivity (%) | 1.1 |
| Nitroethane selectivity (%) | 0.7 |
| 1-nitropropane selectivity (%) | 13.0 |
| 2-nitropropane selectivity (%) | 85.2 |
| 2-nitropropane to 2,2-dinitropropane weight ratio | 61.5 |

Example 4

Propane Nitration with Nitroparaffins in the Reactor Feed

Propane is reacted with 20 weight percent aqueous nitric acid with the above described reactor at a reactor pressure of 1400 psi (96.7 atm), a reaction temperature of 285° C., a residence time of 153 seconds, and a propane to nitric acid mole ratio of 1.82:1. The feed composition and the reaction product stream composition are summarized in Table 7.

TABLE 7

Feed composition and reaction product stream composition

| Component | Feed (g) | Reaction Product (g) |
|---|---|---|
| Propane | 1343 | 906 |
| Nitric Acid | 1054 | 21.1 |
| Water | 3875 | 4447 |
| Acetic Acid | 144 | 249 |
| Acetone | 1.4 | 15.4 |
| Nitromethane | 4.3 | 14.8 |
| Nitroethane | 1.0 | 6.5 |
| 2-nitropropane | 49.3 | 558 |
| 1-nitropropane | 6.3 | 89 |
| 2,2-dinitropropane | 0.3 | 8.8 |
| Nitric oxide | 0 | 43.5 |
| Nitrous oxide | 0 | 6.9 |
| Nitrogen | 0 | 72.0 |
| Carbon monoxide | 0 | 16.4 |
| Carbon dioxide | 0 | 28.1 |

Key performance metrics for this reaction are summarized in Table 8.

TABLE 8

Key performance metrics for nitration of propane with nitroparaffins in the reactor feed

| | |
|---|---|
| Nitric acid conversion (%) | 98.0 |
| Propane conversion (%) | 32.5 |
| Nitric acid yield | 1.55 |
| Propane yield | 0.71 |
| Nitromethane selectivity (%) | 1.7 |
| Nitroethane selectivity (%) | 0.9 |
| 1-nitropropane selectivity (%) | 13.3 |
| 2-nitropropane selectivity (%) | 82.7 |
| 2-nitropropane to 2,2-dinitropropane weight ratio | 59.5 |

A comparison of Table 6 (no nitroparaffins in the reactor feed) with Table 8 (nitroparaffins in the reactor feed) shows that the weight ratio of 2-nitropropane to 2,2-dinitropropane does not significantly change when nitroparaffins are present in the reactor feed, as when an aqueous recycle scheme is used. This indicates that 2-nitropropane in the reactor feed does not further react to form 2,2-dinitropropane to any appreciable extent. The nitric acid and propane yields also do not change (within measurement accuracy). Examples 3 and 4 illustrate that the presence of nitroparaffins in the reactor feed, as in an aqueous recycle process, does not significantly affect the 2-nitropropane selectivity.

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A process for synthesizing at least one nitroalkane, the process comprising:
    reacting a hydrocarbon feedstock with aqueous nitric acid in a reactor at a reactor pressure and a reaction temperature, such that a product stream comprising nitrated compounds and byproducts is formed;
    separating the product stream into at least an oil phase, a gas phase, and an aqueous phase, wherein the oil phase and the aqueous phase contain nitrated compounds;
    dividing the aqueous phase into a first aqueous stream and a second aqueous stream upstream of an absorber;
    returning the first aqueous stream to the reactor;
    supplying the second aqueous stream to the absorber; and
    recovering the at least one nitroalkane from at least one of the oil phase and the second aqueous stream.

2. A process according to claim 1 further comprising:
    absorbing water-soluble and oil-soluble components from the gas phase to form a gas-recovered mixture;
    separating a gas-recovered aqueous phase from the gas-recovered mixture; and
    introducing the gas-recovered aqueous phase to a stripping apparatus to recover the at least one nitroalkane.

3. A process according to claim 1 wherein between about 65 and 85 percent of the aqueous phase is divided into the first aqueous stream.

4. A process according to claim 1 wherein the aqueous nitric acid is added to the reactor at a 10 to 50 weight percent solution.

5. A process according to claim 4 wherein the aqueous nitric acid is added to the reactor at a 15 to 40 weight percent solution.

6. A process according to claim 5 wherein the aqueous nitric acid is added to the reactor at a 18 to 35 weight percent solution.

7. A process according to claim 1 wherein the molar ratio of hydrocarbon to nitric acid is at least about 1.2:1.

8. A process according to claim 1 wherein the reactor pressure is at least about 1000 psi.

9. A process according to claim 1 wherein the reaction temperature is between about 215 and 325 degrees Celsius.

10. A process according to claim 1 wherein the reaction temperature is greater than 230 degrees Celsius.

11. A process according to claim 1 wherein the reaction temperature is 290 degrees Celsius or less.

12. A process according to claim 1 wherein the reactor is a downflow configured reactor.

13. A process according to claim 1 wherein the reactor is a packed reactor.

14. A process according to claim 1 wherein the reactor is an un-packed reactor.

15. The process according to claim 1, wherein the at least one nitroalkane is 2-nitropropane.

16. The process according to claim 1, wherein the at least one nitroalkane is 2,2-nitropropane.

17. A process for synthesizing at least one nitroalkane, the process comprising:
    reacting a hydrocarbon feedstock with aqueous nitric acid in a reactor at a reactor pressure and a reaction temperature, such that a product stream of nitrated compounds and byproducts is formed;
    quenching the product stream to separate the product stream into at least an oil phase, a gas phase, and an aqueous phase;
    dividing the aqueous phase into a first aqueous stream and a second aqueous stream upstream of an absorber;
    returning the first aqueous stream to the reactor;
    supplying the second aqueous stream to the absorber;
    combining the oil phase, the gas phase, and the second aqueous stream in the absorber;
    absorbing water-soluble and oil-soluble components from the gas phase into the oil phase and the second aqueous stream to form a gas-recovered mixture;
    separating a gas-recovered aqueous phase from the gas-recovered mixture; and
    recovering the at least one nitroalkane from at least one of the oil phase and the second aqueous stream.

* * * * *